United States Patent
Sheraton et al.

(10) Patent No.: US 6,795,722 B2
(45) Date of Patent: Sep. 21, 2004

(54) ELECTRODE SENSOR PACKAGE AND APPLICATION TO THE SKIN OF A NEWBORN OR INFANT

(75) Inventors: David A. Sheraton, Lake Forest, CA (US); Arnold M. Heyman, Los Angeles, CA (US); Craig McCrary, Valencia, CA (US)

(73) Assignee: Neotech Products, Inc., Chatsworth, CA (US)

( * ) Notice: Subject to any disclaimer, the term of this patent is extended or adjusted under 35 U.S.C. 154(b) by 62 days.

(21) Appl. No.: 10/174,908

(22) Filed: Jun. 17, 2002

(65) Prior Publication Data

US 2003/0009097 A1 Jan. 9, 2003

Related U.S. Application Data

(60) Provisional application No. 60/298,394, filed on Jun. 18, 2001.

(51) Int. Cl.[7] ............................................. A61B 5/0402
(52) U.S. Cl. ...................... 600/391; 600/392; 600/393; 607/149; 607/152
(58) Field of Search ................................ 600/391–393; 607/149, 152, 153

(56) References Cited

U.S. PATENT DOCUMENTS

| | | | | |
|---|---|---|---|---|
| 3,845,757 A | * | 11/1974 | Weyer | 600/391 |
| 4,365,634 A | * | 12/1982 | Bare et al. | 600/391 |
| 4,370,984 A | * | 2/1983 | Cartmell | 600/385 |
| 4,727,881 A | * | 3/1988 | Craighead et al. | 600/392 |
| 4,736,752 A | * | 4/1988 | Munck et al. | 607/152 |
| 4,979,517 A | * | 12/1990 | Grossman et al. | 607/153 |
| 5,205,297 A | | 4/1993 | Montecalvo et al. | |
| 5,402,780 A | * | 4/1995 | Faasse, Jr. | 600/392 |
| 5,904,712 A | * | 5/1999 | Axelgaard | 607/148 |
| 6,263,226 B1 | * | 7/2001 | Axelgaard et al. | 600/391 |
| 6,276,054 B1 | * | 8/2001 | Cartmell et al. | 29/825 |
| 6,418,333 B1 | * | 7/2002 | Axelgaard | 600/391 |

* cited by examiner

Primary Examiner—Lee S. Cohen
(74) Attorney, Agent, or Firm—William W. Haefliger

(57) ABSTRACT

A sensor device in the form of a substantially flat package for receiving and transmitting signals, to be monitored and/or recorded, comprising, in combination a first layer in the form of an annulus having an undersurface to adhere to the skin of a patient; a second layer in the form of a conductive sensing layer peripherally bounded by the first layer and having an undersurface adapted for contact with the skin of the patient; a conductive terminal extending above the second layer in adjacent and conductive relation therewith; a protector extending in shallow dome configuration over the first and second layers and over the terminal; and a conductive lead extending over edges defined by the first and second terminals, and under the protector, for protected contact with the terminal, and to transmit signals for monitoring or recording.

18 Claims, 5 Drawing Sheets

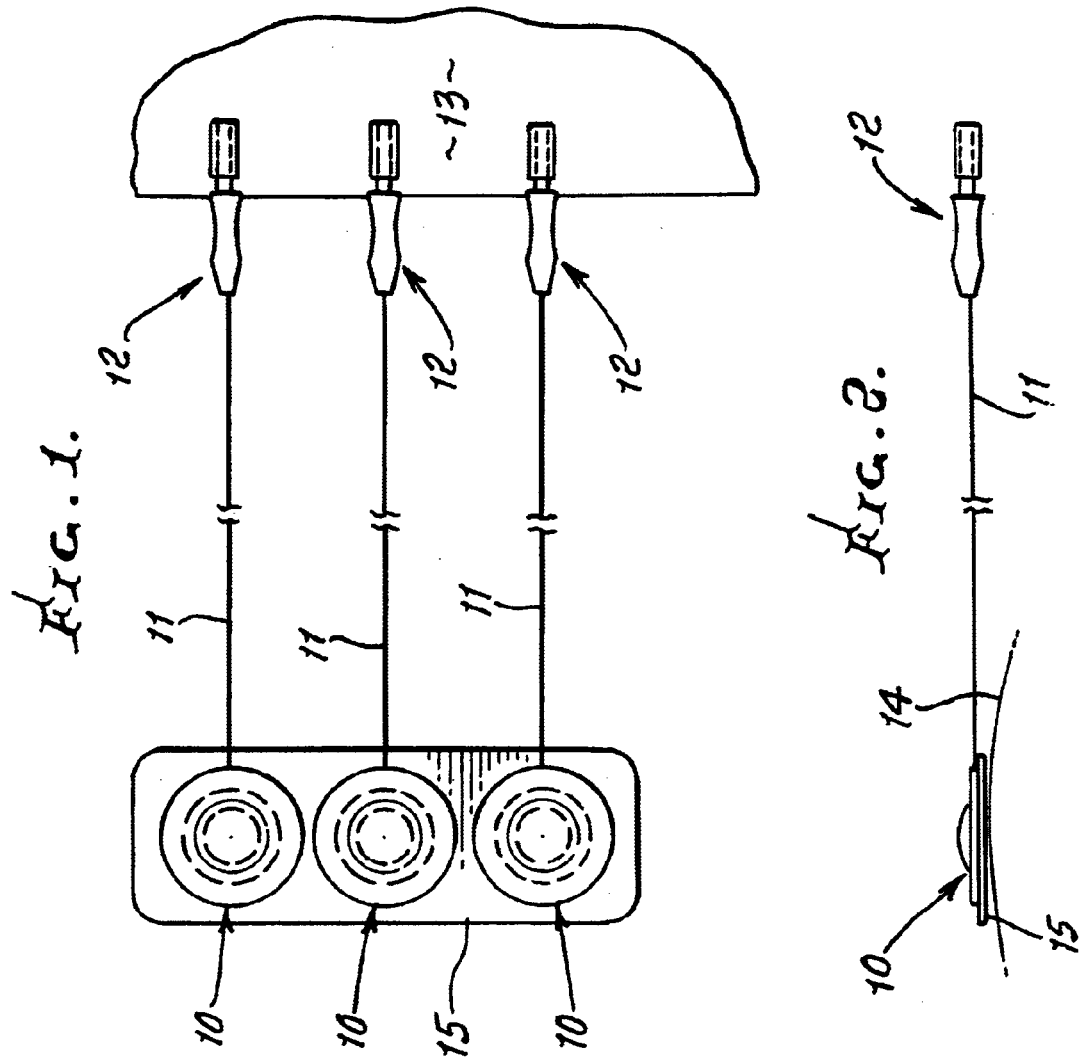

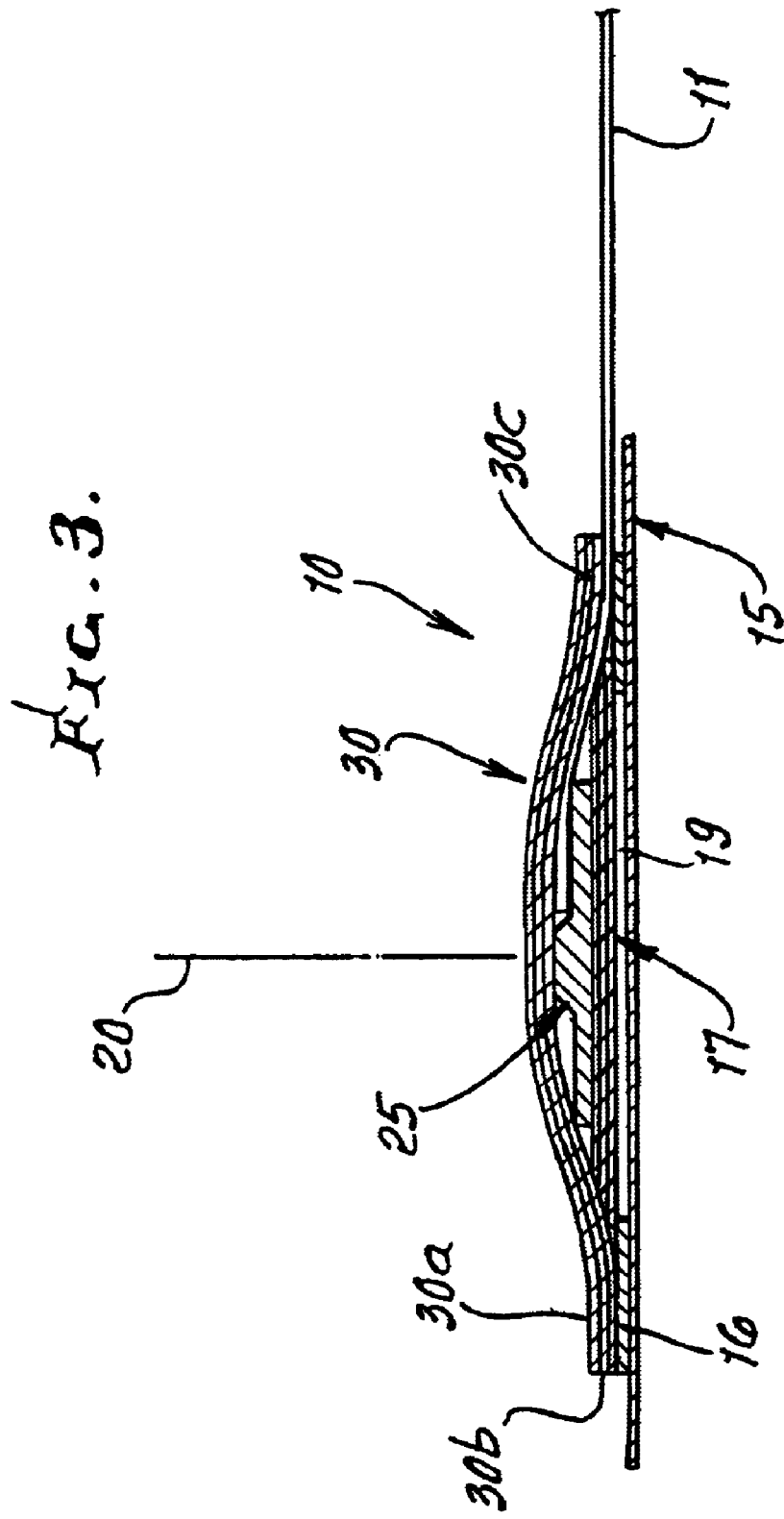

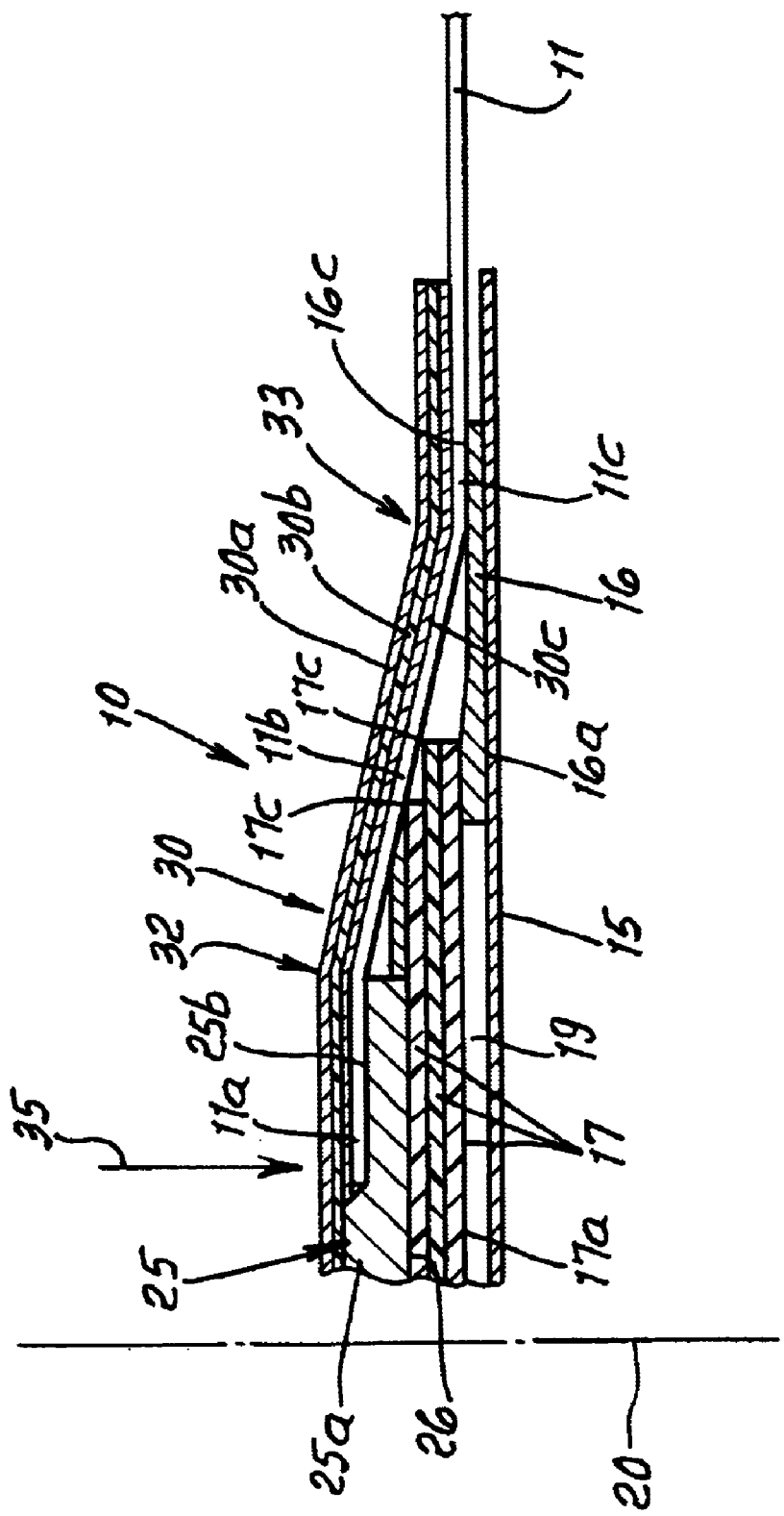

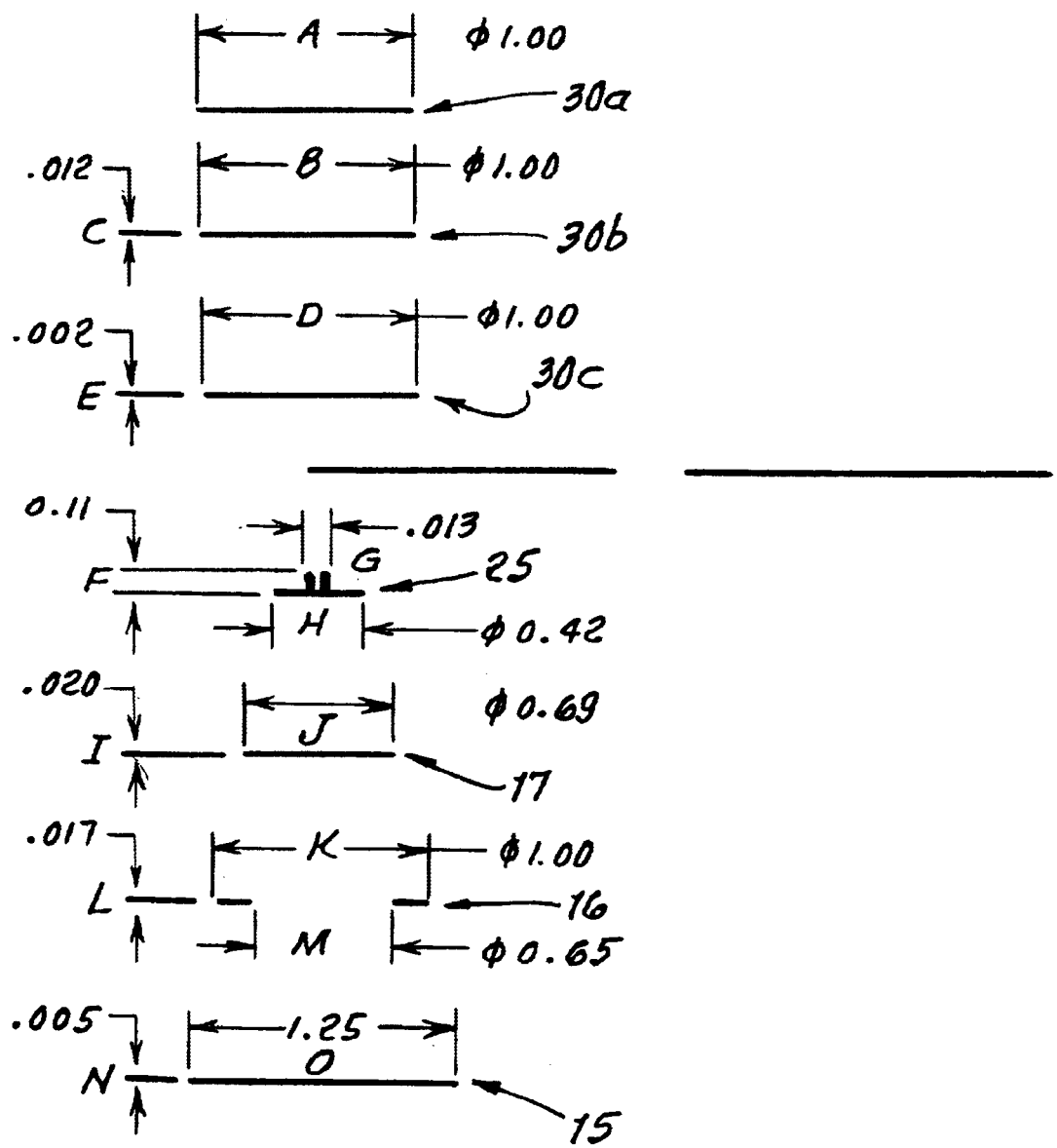

ELECTRODE SENSOR PACKAGE AND APPLICATION TO THE SKIN OF A NEWBORN OR INFANT

This application claims priority over provisional patent application Ser. No. 60/298,394 filed Jun. 18, 2001.

BACKGROUND OF THE INVENTION

This invention relates generally to sensors attachable to the skin of a patient, and more particularly to improvements in sensor packages for topically receiving and transmitting physiologic signals such as electrical activity in a patient, to be monitored or recorded.

There is need for improvements in such devices, particularly as related to achieving flat package configurations, skin protection, improved adhesion to fragile skin, protection of electrical components, capability to efficiently receive signals from the body, via the skin, in a non-invasive manner, for monitoring or recording, and ease and reliability of use, as well as other objectives and advantages in construction, as will be seen.

SUMMARY OF THE INVENTION

It is a major object of the invention to provide improvements in such sensor packages and their use meeting the above needs.

Basically, the sensor package of the invention comprises, in combination:

a) a first layer in the form of an annulus having an undersurface to adhere to the skin of a patient, b) a second layer in the form of a conductive sensing layer, such as a gel layer, peripherally bounded by the first layer and having an undersurface adapted for contact with the skin of the patient, c) a conductive terminal extending above the second layer in adjacent and conductive relation therewith, d) a protector extending in shallow dome configuration over said first and second layers and over the terminal, e) and a conductive lead extending over edges defined by the first and second terminals, and under the protector, for protected contact with the terminal.

As will appear the protector may be located to hold the layers in position, for operation.

A further object is to provide for a disposable protective package configuration wherein the second layer undersurface may be spaced above a lower annular surface defined by the first layer. This packaging enhances maintenance of protection for that undersurface prior to use in contact with the skin. A strip-off protective layer is typically removably attached to the first layer lower annular undersurface, to protect the second layer sensitive undersurface.

Yet another object is to provide the protector in the form of multiple protective layers having multiple functions.

An additional object is to provide the first layer in the form of a hydrocolloid substance, and the second layer in the form of a gel.

These and other objects and advantages of the invention, as well as the details of an illustrative embodiment, will be more fully understood from the following specification and drawings, in which:

DRAWING DESCRIPTION

FIG. 1 is a plan view showing multiple sensor packages, and associated electrical leads;

FIG. 2 is a side elevation view of one of the FIG. 1 sensor packages, and lead;

FIG. 3 is an enlarged vertical section taken in elevation through one of the sensor packages;

FIG. 4 is an enlarged fragmentary view taken in section through the FIG. 3 package;

FIG. 6 is a diagram showing typical dimensions of the FIG. 4 package components.

DETAILED DESCRIPTION

Figure 5:
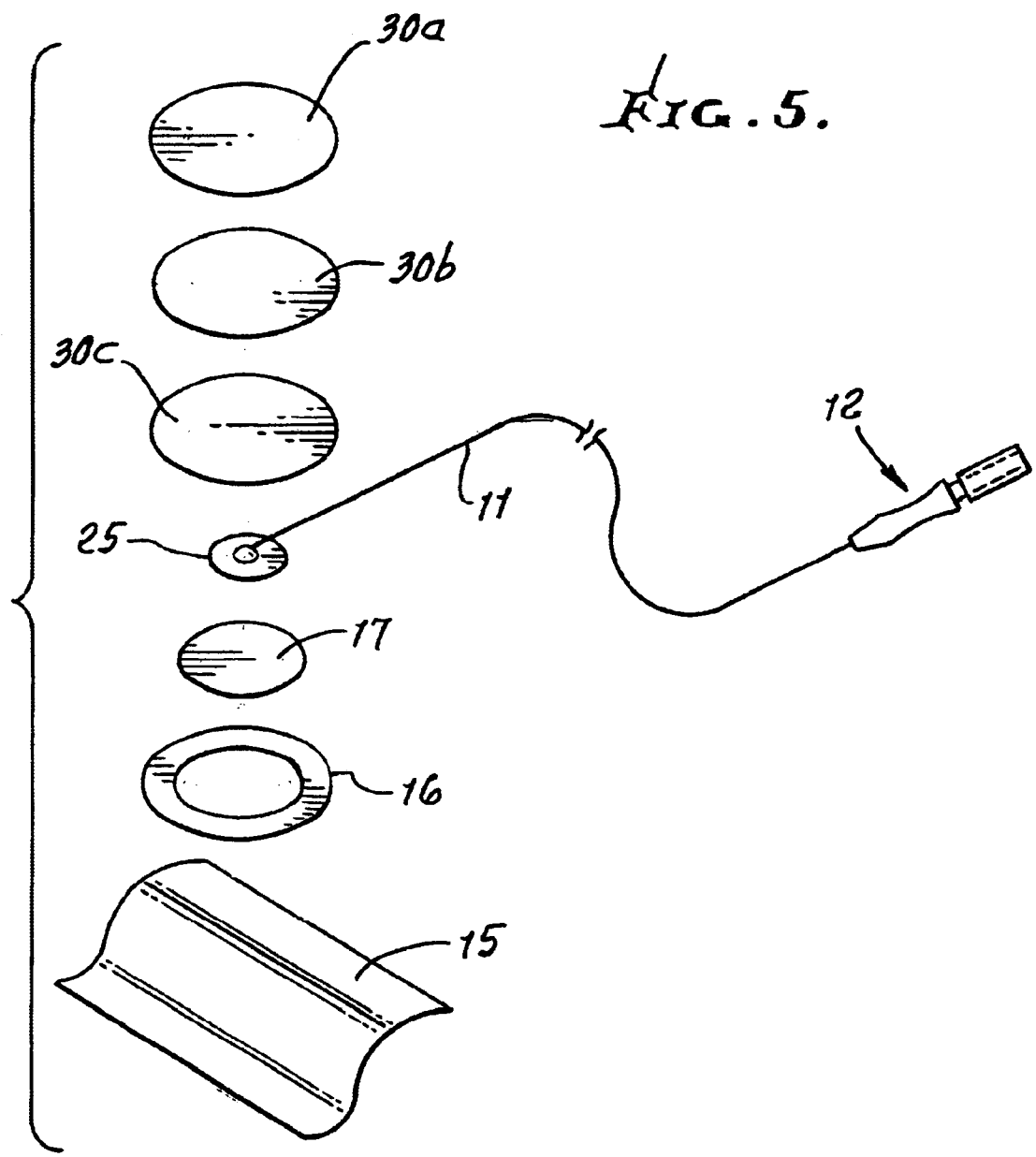
FIG. 5 is an exploded view showing the configuration of the FIG. 3 sensor package preferred components.

FIG. 1 shows three sensor means, in the form of packages or assemblies 10 for receiving and transmitting signals such as cardiac electrical impulses or signals, to be monitored and/or recorded. A lead 11 extends from each package to a terminal plug 12. Numeral 13 represents a signal monitoring or recording apparatus for receiving the sensor signals via leads 11 and plugs 12. FIG. 2 shows a package 10 to be applied to the skin of a patient 14, as after strip-off removal of a protective layer 15.

Referring to FIGS. 3 and 4, the package 10 includes a first layer 16 as for example in the form of an annulus extending about a central axis 20, and having an undersurface 16a to adhere to the patient's skin 14 under manual pressure transmission. The annulus 16 preferably comprises a hydrocolloid material, such material being known.

Examples are:

DuoDerm CGF Control Formula Dressing

Cutinova Hydro

3M Tegasorb Hydrocolloid Dressing

Replicare

Package 10 also includes a second layer or stacked layers 17 in the form of sensing gel material, peripherally bounded by layer 16, but offset upwardly from the plane of 16. The gel may be electrically conductive. Typically layers 17 are mutually adherent at their interfaces. The lowermost layer 17 has an undersurface 17a adapted for contact with the skin of the patient, via space 19 below 17a and bounded by annulus 16. If desired, the lowermost layer 17 may be located in space 19. Space 19, if present, assures that the first layer 16 will annularly contact the patient's skin without interference from undersurface 17a, considering that the skin may not necessarily be locally flat (but may be typically upwardly convex) at the locus of application of the package to the skin. The gel material of 17 is known as Hydrogel and known examples of such material are identified as follows:

Hypergel

Intra Site Gel

Normlgel

MKM Gentell Hydrogel

Also, gap or space 19, if used, protects undersurface 17a from undesirable contact with strip-away protective layer 15. Also space 19 allows movement of the gel layer 17 toward the skin, and relative to the layer 16.

The package 10 also includes a conductive terminal 25 extending above the second layer or layers 17, and in contact with 17 via the interface at 26. The terminal 25 may for example consist of electrically conductive metallic material, such as copper or aluminum, other materials being usable. It has a generally flat configuration, and a raised flat terminal portion 25a to or toward which the end 11a of a lead or wire 11 extends, adjacent the terminal upper surface at 25b. Lead 11 has a portion 11b that slopes downwardly adjacent edge or edges 17c of layer or layers 17, and toward the upper surface 16b of annulus 16, at 11c. From there, the lead extends rightwardly, away from package 10.

Package 10 also includes a multifunction protector 30 extending in protective shallow dome configuration over the terminal 25, over lead portions 11a, 11b and 11g. and over the layers 16 and 17; and protector 30 may typically bond or adhere, annularly, to the upper surface 16 of the hydrocolloidal material of annulus 16. Multiple thin layers of the flexible protector material may be used, and are indicated at 30a, 30b and 30c. The layered or laminar construction of protector 30 facilitates its flexing at regions 32 and 33, and facilitates downward manual pressure transmission to the layer 16, for adhering it to the skin, and downward displacement of the terminal 25 and layer 17 extend under the terminal to pressurably engage undersurface 17a with the skin, in response to manual force transmission indicated by arrow 35. The protector material 30b consists of synthetic resin, such as woven NYLON; protector 30a is typically identifying printing carried by 30k; and material 30c consists of an adhesive layer such as a double sided adhesive strip. Also, layer 30c engages layers 16 and 17 to position them for functioning and to prevent lateral movement on the skin.

FIG. 5 shows the above described elements in exploded view form; and FIG. 6 indicates typical dimensions of the respective elements. Such dimensions have been determined to provide a best results package, in apparatus and use. Other dimensions may be used.

The method of providing and using a sensor package as described, for receiving and transmitting signals, includes:

a) transmitting manually exerted force to said annular first layer 16, via the protective layer 30 to engage the undersurface of the first layer against the skin of a patient, b) transmitting manually exerted force to the second layer 17, via the protective layer 30, to displace a central portion of said second layer undersurface downwardly relative to the first layer, to contact the skin of a patient, c) and sensing signals and transmitting same via said second layer, said terminal and said lead, for monitoring or recording purposes.

After such use, the package is removed from the skin, for disposal.

In FIG. 6, dimensions A to O are as indicated, in inches.

We claim:

1. A sensor means in the form of a substantially flat package for receiving and transmitting signals, to be monitored and/or recorded, comprising in combination:

a) a first layer in the form of an annulus having an undersurface to adhere to the skin of a patient, b) a second layer in the form of a conductive sensing layer peripherally bounded by said first layer and having an undersurface exposed downwardly via a space defined by the first layer and adapted for contact with the skin of the patient, c) a conductive terminal extending above the second layer in adjacent and conductive relation therewith, d) a protector extending in shallow dome configuration over said first and second layers and in contact therewith, and over said terminal, as well as over said space.

e) and a conductive lead extending over edges defined by said first and second layers, and under said protector, for protected contact with said terminal.

2. The combination of claim 1 wherein said first layer comprises a hydrocolloid material.

3. The combination of claim 1 wherein said second layer undersurface is spaced above a lower annular surface defined by the first layer.

4. The combination of claim 3 including a strip-off protective layer removably attached to said first layer lower annular surface.

5. The combination of claim 1 wherein said protector has layered configuration.

6. The combination of claim 5 wherein said protector comprises a stack of layers, including:

i) a woven synthetic resin layer, ii) printed material on the resin layer, iii) an adhesive layer underlying the resin layer and adherent to peripheral portions of the first and second layers.

7. The combination of claim 1 including instrumentation in electrical communication with said lead, for monitoring or recording electrical signals indicative of each cardiac activity.

8. The combination of claim 1 wherein the dimensions of said first layer are approximately as follows:

| thickness | .017 inches |
|---|---|
| inner diameter | 0.65 inches |
| outer diameter | 1.00 inch. |

9. The combination of claim 8 wherein the dimensions of said second layer are approximately as follows:

| thickness | .020 inch |
|---|---|
| overall diameter | .069 inch. |

10. The combination of claim 9 wherein the dimensions of said protector are approximately as follows:

| thickness | .026 inch |
|---|---|
| overall diameter | 1.00 inch. |

11. The combination of claim 9 wherein the dimensions of said terminal are approximately as follows:

| thickness | 0.11 inch |
|---|---|
| overall diameter | 0.42 inch. |

12. The method of providing and using the package of claim 1 for receiving and transmitting signals, that includes:

a) transmitting manually exerted force to said first layer, via said protective layer to engage said undersurface of the first layer and the skin of a patient, b) transmitting manually exerted force to said second layer, via said protective layer, to displace a central portion of said second layer undersurface downwardly relative to said first layer to contact the skin of a patient, c) and sensing signals and transmitting same via said second layer, said terminal and said lead, for monitoring or recording.

13. The method of claim 12 including adhering said protector to peripheral portions of said first and second layers to position them transversely relative to an axis defined by the package.

14. A sensor means in the form of a substantially flat package for receiving and transmitting signals, to be monitored and/or recorded, comprising in combination:

a) a first layer having an undersurface to adhere to the skin of a patient,
b) a second layer in the form of a conductive sensing layer peripherally substantially bounded by said first layer and having an undersurface exposed downwardly for contact with the skin of the patient, and free of the first layer,
c) a conductive terminal extending above the second layer in adjacent and conductive relation therewith,
d) a protector having multiple layers extending in shallow dome configuration directly over and in contact with upper surfaces of said first and second layers and over said terminal, as well as completely over said second layer undersurface,
e) and a conductive lead extending over edges defined by said first and second layers, and under said protector, for protected contact with said terminal.

15. The combination of claim 14, in which said first layer comprises a hydrocolloid material, and said second layer undersurface is spaced above a lower surface defined by the first layer.

16. The combination of claim 14 wherein said protector comprises a stack of layers, including:

i) a woven synthetic resin layer,
ii) printed material on the resin layer,
iii) an adhesive layer underlying the resin layer and adherent to peripheral portions of the first and second layers.

17. The combination of claim 16 including instrumentation in electrical communication with said lead, for monitoring or recording electrical signals indicative of each cardiac activity.

18. A sensor means in the form of a substantially flat package for receiving and transmitting signals, to be monitored and/or recorded, comprising in combination:

a) a first layer in the form of an annulus having an undersurface to adhere to the skin of a patient,
b) a second layer in the form of a conductive sensing layer peripherally bounded by said first layer and having an undersurface exposed downwardly via a space defined by the first layer and adapted for contact with the skin of the patient,
c) a conductive terminal extending above the second layer in adjacent and conductive relation therewith,
d) a protector extending in shallow dome configuration over said first and second layers and in retention therewith, and over said terminal, as well as over said space.
e) and a conductive lead extending over edges defined by said first and second layers, and under said protector, for protected contact with said terminal.

* * * * *